United States Patent
Broersen et al.

(10) Patent No.: US 11,141,397 B2
(45) Date of Patent: Oct. 12, 2021

(54) COMPOSITION FOR IMPROVING EFFICACY OF L-DOPA TREATMENT

(71) Applicant: N.V. NUTRICIA, Zoetermeer (NL)

(72) Inventors: Ladislaus Maria Broersen, Utrecht (NL); Nick Van Wijk, Utrecht (NL); Amos Attali, Utrecht (NL)

(73) Assignee: N.V. Nutricia, Zoetermeer (NL)

( * ) Notice: Subject to any disclaimer, the term of this patent is extended or adjusted under 35 U.S.C. 154(b) by 0 days.

(21) Appl. No.: 16/706,337

(22) Filed: Dec. 6, 2019

(65) Prior Publication Data

US 2020/0108036 A1 Apr. 9, 2020

Related U.S. Application Data

(63) Continuation of application No. PCT/NL2017/050382, filed on Jun. 9, 2017.

(51) Int. Cl.
| | |
|---|---|
| *A61K 31/198* | (2006.01) |
| *A61K 31/14* | (2006.01) |
| *A61K 31/202* | (2006.01) |
| *A61K 31/375* | (2006.01) |
| *A61K 31/4415* | (2006.01) |
| *A61K 31/519* | (2006.01) |
| *A61P 25/16* | (2006.01) |
| *A61K 31/7072* | (2006.01) |
| *A61K 31/714* | (2006.01) |
| *A61K 47/24* | (2006.01) |

(52) U.S. Cl.
CPC ............ *A61K 31/198* (2013.01); *A61K 31/14* (2013.01); *A61K 31/202* (2013.01); *A61K 31/375* (2013.01); *A61K 31/4415* (2013.01); *A61K 31/519* (2013.01); *A61K 31/7072* (2013.01); *A61K 31/714* (2013.01); *A61K 47/24* (2013.01); *A61P 25/16* (2018.01)

(58) Field of Classification Search
CPC .............. A61K 31/198; A61K 31/7072; A61K 31/714; A61K 31/519; A61K 47/24; A61K 31/375; A61K 31/14; A61K 31/202; A61K 31/4415; A61P 25/16

USPC ......................................................... 514/51
See application file for complete search history.

(56) References Cited

FOREIGN PATENT DOCUMENTS

| NL | WO2015/084160 | * 11/2015 |
|---|---|---|
| WO | WO-2015/084160 A1 | 6/2015 |
| WO | WO-2015/084161 A1 | 6/2015 |

OTHER PUBLICATIONS

International Preliminary Report on Patentability, issued in International Patent Application No. PCT/NL2017/050382, dated Sep. 19, 2019.
Perez-Pardo, et al. "Promising Effects of Neurorestorative Diets on Motor, Cognitive, and Gastrointestinal Dysfunction after Symptom Development in a Mouse Model of Parkinson's Disease"; Frontiers in Aging Neuroscience, vol. 9; (XP055449592); Mar. 20, 2017.
Perez-Pardo, et al. "Gut-brain and brain-gut axis in Parkinson's disease models: Effects of a uridine and fish oil diet"; Nutritional neuroscience: an international journal of diet, nutrition and the nervous system, pp. 1-12; (XP055449595); Mar. 9, 2017.

* cited by examiner

*Primary Examiner* — Yih-Horng Shiao
(74) *Attorney, Agent, or Firm* — N.V. Nederlandsch Octrooibureau; Catherine A. Shultz; Katelyn J. Bernier

(57) ABSTRACT

The invention pertains to a composition for use in (a) treatment of impaired motor skills in a mammal suffering from Parkinson's Disease; (b) improving the efficacy of levodopa (L-DOPA) in treatment of impaired motor skills in a mammal suffering from Parkinson's Disease; and/or (c) reducing L-DOPA associated side effects, preferably involuntary movements selected from the group consisting of choreiform, dystonic and dyskinetic movements, in the treatment of impaired motor skills in a mammal suffering from Parkinson's Disease, comprising co-administering to the subject L-DOPA and a composition comprising therapeutically effective amounts of: (i) at least one of uridine, cytidine, or salts, phosphates, acyl derivatives or esters thereof; (ii) at least one of docosahexaenoic acid (22:6; DHA), eicosapentaenoic acid (20:5; EPA) and docosapentaenoic acid (22:5; DPA); (iii) choline, or salts or esters thereof; and (iv) at least one vitamin B selected from vitamins B6, B9 and B12.

20 Claims, 1 Drawing Sheet

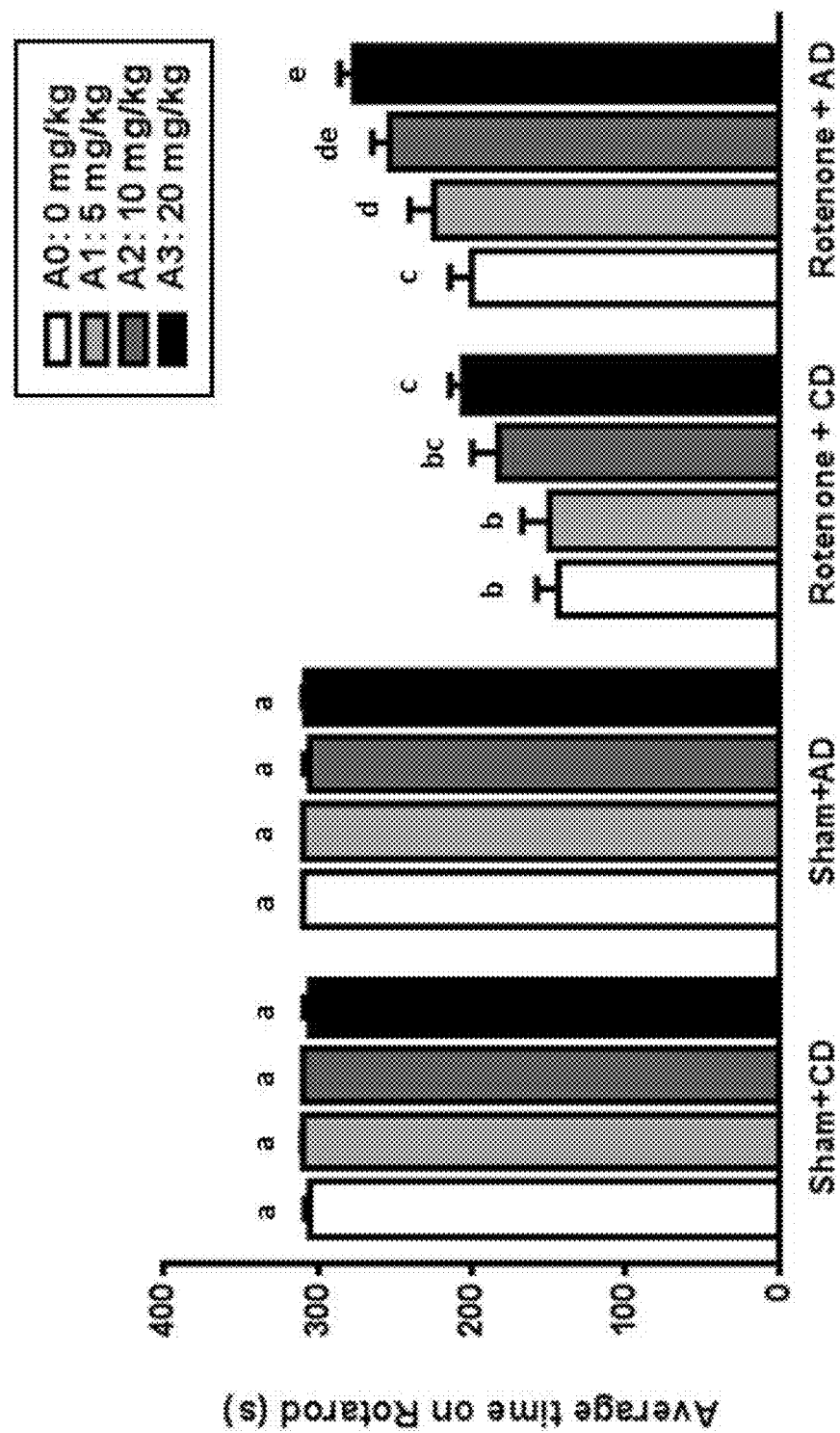

COMPOSITION FOR IMPROVING EFFICACY OF L-DOPA TREATMENT

CROSS-REFERENCE TO RELATED APPLICATIONS

The present application is a Continuation of International Patent Application No. PCT/NL2017/050382, filed Jun. 9, 2017, the entire contents of which are hereby incorporated by reference.

FIELD OF INVENTION

The present invention is in the field of medical nutrition and more particularly relates to nutritional compositions for use in the treatment of Parkinson's Disease.

BACKGROUND ART

Parkinson's disease (PD) clinical picture is usually dominated by motor impairment. However non-motor symptoms, such as cognitive decline and gastrointestinal dysfunctions, may already develop before the motor symptoms and are major determinants of quality of life. L-3,4-di-hydroxy-phenylalanine (levodopa or L-DOPA) is a precursor of the neurotransmitter dopamine that suppresses some of the PD motor symptoms since it compensates for dopaminergic cell loss by enhancing dopamine synthesis in the remaining terminals. Hitherto, the oral supplementation with levodopa is the most efficient drug in the treatment of PD. Between 2001 and 2012, levodopa was used by 85% of patients suffering from PD.

However, this therapy has several side effects, it does not prevent dopaminergic neuron degeneration, and many of the non-motor symptoms are unresponsive to levodopa. Some simple side effects of levodopa like nausea and vomiting are typically reduced by the combined administration of a peripheral decarboxylase inhibitor such as benserazide or carbidopa. Serious motor-related (non-gastrointestinal) side effects most frequently reported that come with prolonged use of levodopa include involuntary movements and mental status changes (in as many as 50% of patients treated on long-term therapy). The types of involuntary movements due to levodopa have been characterized as choreiform, dystonic and dyskinetic.

Choreiform movements due to levodopa therapy may occur in as many as 80% of patients treated for one year and frequently involve facial grimacing, exaggerated chewing, and twisting and protrusion of the tongue. Several types of motor fluctuations may occur and result in "bradykinetic episodes". Some motor fluctuations are related to the timing of dosage administration. For example, patients may experience "peak-of-the-dose dyskinesia" and a wearing-off effect called "end-of-the-dose akinesia". The "wearing-off effect may result in early morning dystonia. Such motor fluctuations may be managed by increasing the frequency of dosage administration and decreasing the dose administered to achieve a smoother therapeutic effect. Other motor fluctuations are not related to the timing of dose administration. Such fluctuations are characterized by sudden loss of levodopa effect which may last for minutes to hours and result in akinesia followed by a sudden return of levodopa effect. These "on-off" fluctuations may occur many times per day. "On-off" fluctuations may respond to more frequent dose administration. These side effects come with long-term use of levodopa and the solution practiced in the art is to dose more frequent and/or higher. This however only adds more issues, in patients that have more and more intestinal problems leading to reduced uptake of levodopa.

In that context, there is a great need for additional therapies that reduce/modulate both motor and non-motor symptoms and can reduce levodopa dependency.

SUMMARY OF THE INVENTION

The inventors investigated the effects of combined oral administration of a specific dietary intervention together with levodopa treatment in C57BL/6J mice which were injected with rotenone or vehicle in the striatum. The diet intervention started four weeks after surgery when PD-like symptoms had developed. The effects of oral treatment with different doses of levodopa were assessed weekly. The results reported in FIG. 1 showed that rotenone-induced rotarod performance problems were alleviated by the levodopa and therapeutic dietary intervention together to the extent that the effects were as effective as a 400% higher levodopa treatment alone.

The invention thus pertains to a composition for use in:
(a) treatment of impaired motor skills (i.e. treatment of impaired motor symptoms) in a mammal suffering from Parkinson's Disease;
(b) improving the efficacy of levodopa (L-DOPA) in treatment of impaired motor skills (i.e. treatment of impaired motor symptoms) in a mammal suffering from Parkinson's Disease; and/or
(c) reducing L-DOPA associated side effects in the treatment of impaired motor skills (i.e. treatment of impaired motor symptoms) in a mammal suffering from Parkinson's Disease, comprising co-administering to the subject L-DOPA and a composition comprising therapeutically effective amounts of:
  (i) at least one of uridine, cytidine, or salts, phosphates, acyl derivatives or esters thereof;
  (ii) at least one of docosahexaenoic acid (22:6; DHA), eicosapentaenoic acid (20:5; EPA) and docosapentaenoic acid (22:5; DPA);
  (iii) choline, or salts or esters thereof; and
  (iv) at least one vitamin B selected from vitamins B6, B9 and B12.

The invention also pertains to a method for (a), (b) and/or (c) as defined here above, said method comprising co-administering to the subject L-DOPA and a composition comprising therapeutically effective amounts of (i)-(iv) as detailed here above, optionally comprising further ingredients such as described below. The invention also pertains to the use of such composition in the manufacture of a product for (a), (b) and/or (c) as defined here above.

The side effects reduced using the composition of the invention are undesired motor symptoms or involuntary movements, preferably involuntary movements selected from the group consisting of choreiform, dystonic and dyskinetic movements associated with chronic levodopa administration. Treatment of impaired motor skills preferably involves or includes improving motor coordination and balance, and equilibrioception.

BRIEF DESCRIPTION OF THE DRAWINGS

FIG. 1 shows the effects of dietary intervention and different levodopa doses on rotarod performance.

The present invention will be discussed in more detail below, with reference to the figure which shows the effects of the dietary intervention and different levodopa doses on rotarod performance, in terms of maintaining postural balance and motor coordination to prevent falling from the rotating rod before the end of the trial, i.e. within 300 sec. Both levodopa and dietary treatments alleviated rotenone-induced motor dysfunction. The combined administration of the diet and levodopa showed additive beneficial effects on rotarod performance. Data are shown as mean±SEM. Different letters indicate mean values were significantly different ($p<0.05$, bars with the same letters are statistically equal).

From the figure it can be concluded that the effect of a combination of 5 mg/kg levodopa and the intervention was as at least as effective as 20 mg/kg levodopa alone, i.e. resulting in at least 400% improved efficacy. In fact the efficacy of co-administration is most likely even higher, considering that 0 mg/kg of levodopa in animals on the Active diet (AD) was as effective as 20 mg/kg of levodopa in animals on the Control diet (CD), and that 5 mg/kg of levodopa in animals on AD (letter d) was more effective than 20 mg/kg of levodopa in animals on CD (letter c).

LIST OF EMBODIMENTS

1. A composition for use in (a) treatment of impaired motor skills in a mammal suffering from Parkinson's Disease; (b) improving the efficacy of levodopa (L-DOPA) in treatment of impaired motor skills in a mammal suffering from Parkinson's Disease; and/or (c) reducing L-DOPA associated side effects, preferably involuntary movements selected from the group consisting of choreiform, dystonic and dyskinetic movements, in the treatment of impaired motor skills in a mammal suffering from Parkinson's Disease, comprising co-administering to the subject L-DOPA and a composition comprising therapeutically effective amounts of:
   (i) at least one of uridine, cytidine, or salts, phosphates, acyl derivatives or esters thereof;
   (ii) at least one of docosahexaenoic acid (22:6; DHA), eicosapentaenoic acid (20:5; EPA) and docosapentaenoic acid (22:5; DPA);
   (iii) choline, or salts or esters thereof; and
   (iv) at least one vitamin B selected from vitamins B6, B9 and B12.
2. The composition for use according to embodiment 1, wherein the dosage of L-DOPA is reduced with more than 50% compared to the dosage when the composition is not co-administered.
3. The composition for use according to any of the preceding embodiments, wherein the subject is a PD patient who has started to receive L-DOPA prescription less than 5 years before the start of said co-administration, more preferably less than 3 years before, more preferably less than 2 years before, most preferably less than 1 years before the start of said co-administration.
4. The composition for use according to any of the preceding embodiments, wherein the treatment of impaired motor skills involves or includes improving motor coordination and balance, and stimulating equilibrioception.
5. The composition for use according to any one of the preceding embodiments, comprising (iv) at least two vitamins B selected from vitamins B6, B9 and B12.
6. The composition for use according to embodiment 5, comprising (iv) vitamins B6, B9 and B12.
7. The composition for use according to any one of the preceding embodiments, comprising therapeutically effective amounts of (v) dietary fiber, preferably butyrate-producing fibre.
8. The composition for use according to any one of the preceding embodiments, comprising therapeutically effective amounts of (vi) vitamin D.
9. The composition for use according to any one of the preceding embodiments, comprising 500 - 5000 mg DHA+EPA per day.
10. The composition for use according to any one of the preceding embodiments wherein the composition provides 0.1 to 6 g per day of one or more of uridine, cytidine, or salts, phosphates or esters thereof, calculated as uridine and cytidine, preferably 0.1-6 g per day of one or more of uridine or salts, phosphates or esters thereof, calculated as uridine.
11. The composition for use according to any one of the preceding embodiments, wherein the composition provides, per day, more than 50 mg of choline, or salts or esters thereof, calculated as choline.
12. The composition for use according to any one of the preceding embodiments, wherein the composition further comprises therapeutically effective amounts of at least one and more preferably at least two antioxidants selected from vitamin C, vitamin E and selenium.
13. The composition for use according to any one of the preceding embodiments, wherein the composition further comprises at least one phospholipid.
14. The composition for use according to any one of the preceding embodiments, wherein the composition comprises, per 125 ml of liquid:
   200-900 mg, preferably 300-800 mg EPA;
   900-1500 mg, preferably 950-1300 mg DHA;
   50-600 mg, preferably 60-200 mg phospholipids;
   200-600 mg, preferably 300-500 mg choline;
   400-800 mg, preferably 500-700 mg uridine and/or UMP;
   20-60 mg, preferably 30-50 mg vitamin E (alpha-TE);
   60-100 mg, preferably 60-90 mg vitamin C;
   40-80 μg, preferably 45-65 μg selenium;
   1-5 μg, preferably 2-4 μg vitamin B12;
   0.5-3 mg, preferably 0.5-2 mg vitamin B6; and
   200-600 μg, preferably 300-500 μg folic acid.
15. Use of a composition in the manufacture of a product for use in (a) treatment of impaired motor skills in a mammal suffering from Parkinson's Disease; (b) improving the efficacy of levodopa (L-DOPA) in treatment of impaired motor skills in a mammal suffering from Parkinson's Disease; and/or (c) reducing L-DOPA associated side effects, preferably involuntary movements selected from the group consisting of choreiform, dystonic and dyskinetic movements, in the treatment of impaired motor skills in a mammal suffering from Parkinson's Disease, said use comprising co-administering to the subject L-DOPA and a composition comprising therapeutically effective amounts of:
   (i) at least one of uridine, cytidine, or salts, phosphates, acyl derivatives or esters thereof;
   (ii) at least one of docosahexaenoic acid (22:6; DHA), eicosapentaenoic acid (20:5; EPA) and docosapentaenoic acid (22:5; DPA);
   (iii) choline, or salts or esters thereof; and
   (iv) at least one vitamin B selected from vitamins B6, B9 and B12.
16. Use according to embodiment 15, wherein the dosage of L-DOPA is reduced with more than 50% compared to the dosage of L-DOPA if the composition is not co-administered.
17. Use according to embodiment 15 or 16, wherein the subject is a PD patient who has started to receive L-DOPA prescription less than 5 years before the start of said co-administration, more preferably less than 3 years before, more preferably less than 2 years before, most preferably less than 1 years before the start of said co-administration.

18. Use according to any of embodiments 15-17, wherein the treatment of impaired motor skills involves or includes improving motor coordination and balance, and stimulating equilibrioception.

19. Use according to any of embodiments 15-18, comprising (iv) at least two vitamins B selected from vitamins B6, B9 and B12, preferably comprising (iv) vitamins B6, B9 and B12.

20. Use according to any of embodiments 15-19, comprising therapeutically effective amounts of (v) dietary fiber, preferably butyrate-producing fibre.

21. Use according to any of embodiments 15-20, comprising therapeutically effective amounts of (vi) vitamin D.

22. A method for (a) treatment of impaired motor skills in a mammal suffering from Parkinson's Disease; (b) improving the efficacy of levodopa (L-DOPA) in treatment of impaired motor skills in a mammal suffering from Parkinson's Disease; and/or (c) reducing L-DOPA associated side effects, preferably involuntary movements selected from the group consisting of choreiform, dystonic and dyskinetic movements, in the treatment of impaired motor skills in a mammal suffering from Parkinson's Disease, said method comprising co-administering to the subject L-DOPA and a composition comprising therapeutically effective amounts of:
   (i) at least one of uridine, cytidine, or salts, phosphates, acyl derivatives or esters thereof;
   (ii) at least one of docosahexaenoic acid (22:6; DHA), eicosapentaenoic acid (20:5; EPA) and docosapentaenoic acid (22:5; DPA);
   (iii) choline, or salts or esters thereof; and
   (iv) at least one vitamin B selected from vitamins B6, B9 and B12.

23. A kit of parts comprising:
(a) L-DOPA; and
(b) a composition comprising therapeutically effective amounts of:
   (i) at least one of uridine, cytidine, or salts, phosphates, acyl derivatives or esters thereof;
   (ii) at least one of DHA, EPA and DPA, preferably at least one of DHA and EPA;
   (iii) choline, or salts or esters thereof; and
   (iv) at least one, preferably at least two of vitamin B selected from vitamins B6, B9 and B12.

24. The kit according to embodiment 23, said composition (b) further comprising therapeutically effective amounts of (v) dietary fiber, preferably butyrate-producing fibre.

25. The kit according to embodiment 23 or 24, said composition (b) further comprising therapeutically effective amounts of (vi) vitamin D.

DETAILED DESCRIPTION OF EMBODIMENTS

L-3,4-di-hydroxy-phenylalanine (levodopa or L-DOPA) is a precursor of the neurotransmitter dopamine that suppresses some of the PD motor symptoms. Daily dosages of such medication are readily available to the skilled person, reference is for instance to the Parkinson Foundation (http://wwww.toolkitparkinson.org/content/levodopa). It is an aim to improve the efficacy of L-DOPA on motor function, particular on motor coordination, balance and equilibrioception such that in case of co-administration of L-DOPA with the composition according to the invention the L-DOPA (daily) dosage can preferably be lowered to more than 50%, preferably more than 60%, more preferably more than 70% compared to the L-DOPA dosage if not co-administered with the composition of the invention.

It is preferred that the mammal received oral levodopa treatment.

The method or use may further involve co-administering the composition of the invention, and levodopa with therapeutically effective amounts of a peripheral decarboxylase inhibitor (such as carbidopa or benserazide) that is typically used to decrease the breakdown of levodopa in the periphery and thus increasing its availability in the central nervous system/brain, where it is metabolized into dopamine. In the art, benserazide is also claimed to reduce side-effects of levodopa (such as nausea) and to increase the efficacy of levodopa so that the daily dose can be reduced. In the experiments attached benserazide was administered in all groups receiving L-DOPA, and the improved efficacy induced by the composition of the invention is thus observed on top of any asserted efficacy improvements in terms of L-DOPA efficacy already achieved with benserazide.

The term 'co-administration' means that the composition and levodopa are both administered daily, which in one embodiment can be simultaneously or sequentially in any order. Levodopa is typically administered several times a day, while the composition of the invention is preferably administered once or twice per day, preferably once a day. In one embodiment, the composition of the invention is administered at least once daily, regardless the timing of levodopa administration, provided that levodopa is prescribed on a daily basis.

The composition of the invention is preferably intended for oral administration.

The mammal suffering from Parkinson's Disease [PD] is preferably a human person. The person is preferably an early PD patient, i.e. newly diagnosed or prodromal PD patient, preferably a PD patient who has started to receive levodopa prescription less than 5 years before, more preferably less than 3 years before, more preferably less than 2 years before, most preferably less than 1 year before. In any case, it is preferred that the composition of the invention is co-administered with levodopa before the end of the so-called (motor) honeymoon (or 'levopdopa honeymoon') period which is typically a 3-5 year period from the start of levodopa treatment in which the Parkinson's motor symptoms are adequately controlled with levodopa, while the side effects and particularly the aforementioned involuntary movements of levodopa treatment are not too disabling. Reference is made to https://www.agingcare.com/articles/farewell-parkinsons-honeymoon-167436.htm. Due to the additive effects of the combination of the present invention with the drug it is possible to reduce levodopa doses given to patients, reducing the negative secondary effects and contributing to a longer beneficial use of the drug. In one embodiment, the PD patient is a drug naive patient starting with levodopa treatment.

In one aspect of the present invention, the composition according to the invention may be used as a pharmaceutical product comprising one or more pharmaceutically acceptable carrier materials.

In another aspect of the present invention, the composition according to the invention may be used as a nutritional product, for example as a nutritional supplement, e.g., as an additive to a normal diet, as a fortifier, to add to a normal diet, or as a complete nutrition.

The pharmaceutical product, preferably for enteral application, may be a solid or liquid galenical formulation. Examples of solid galenical formulations are tablets, capsules (e.g. hard or soft shell gelatine capsules), pills, sachets, powders, granules and the like which contain the active ingredient together with conventional galenical carriers. Any conventional carrier material can be utilized. The carrier material can be organic or inorganic inert carrier material suitable for oral administration. Suitable carriers include water, gelatine, gum Arabic, lactose, starch, magnesium stearate, talc, vegetable oils, and the like. Additionally, additives such as flavouring agents, preservatives, stabilizers, emulsifying agents, buffers and the like may be added in accordance with accepted practices of pharmaceutical compounding.

If the composition is a pharmaceutical product, such product may contain the daily dosage in one or more dosage units. The dosage unit may be in a liquid form or in a solid form, wherein in the latter case the daily dosage may be provided by one or more solid dosage units, e.g. in one or more capsules or tablets.

In one aspect of the present invention, the composition according to the invention may be used in a nutritional product comprising components selected from the group of fats, proteins, and carbohydrates. It is understood that a nutritional product differs from a pharmaceutical product by the presence of nutrients which provide nutrition to the subject to which the composition is administered, in particular the presence of protein, fat, digestible carbohydrates and dietary fibres. It may further contain ingredients such as minerals, further vitamins, organic acids, and flavouring agents. Although the term "nutraceutical product" is often used in literature, it denotes a nutritional product with a pharmaceutical component or pharmaceutical purpose. Hence, the nutritional composition according to the invention may also be used in a nutraceutical product.

The product of the invention is an enteral composition, intended for oral administration. It is preferably administered in liquid form. In one embodiment, the product comprises a lipid fraction and at least one of carbohydrates and proteins, wherein the lipid composition provides between 20 and 50 energy % of the food product. This is based on the assumption that lipid, carbohydrates and protein generate approximately 9, 4 and 4 kcal/g, respectively, the 3 together making up for all caloric contributions of the composition. In one embodiment, the food product is a liquid composition containing between 0.8 and 1.4 kcal per ml.

DHA/EPA/DPA

The method, product, composition or kit of the invention comprises therapeutically effective amounts of at least one omega-3 long-chain polyunsaturated fatty acid (LC-PUFA; having a chain length of 18 and more carbon atoms) selected from the group consisting of docosahexaenoic acid (22:6, ω-3; DHA), eicosapentaenoic acid (20:5, ω-3; EPA) and docosapentaenoic acid (22:5 ω-3; DPA), preferably at least DHA and/or EPA, more preferably at least DHA, most preferably DHA and EPA. EPA is converted to DPA (ω-3), increasing subsequent conversion of DPA to DHA in the brain. EPA is also believed to play an important role in controlling inflammatory processes in Parkinson's Disease. Hence, the present composition preferably contains a significant amount of EPA.

The DHA, EPA and/or DPA are preferably provided as triglycerides, diglycerides, monoglycerides, free fatty acids or their salts or esters, phospholipids, lysophospholipids, glycerol ethers, lipoproteins, ceramides, glycolipids or combinations thereof. Preferably, the present composition comprises at least DHA in triglyceride form, more preferably DHA and EPA. Suitable ω-3 LCPUFA and/or DHA/EPA sources include tuna oil, (other) fish oils, DHA-rich alkyl esters, algae oil, egg yolk, or phospholipids enriched with ω-3 LCPUFA e.g. phosphatidylserine-DHA. Preferably, a product, composition or kit according to the invention comprises fish oil providing the omega-3 LCPUFA(s). Another particularly suitable source for the omega-3 LCPUFA(s) is algae oil.

In terms of daily dosage, the present method preferably comprises the administration of 500 to 5000 mg DHA+EPA+DPA per day. In a preferred embodiment, in terms of daily dosage, the present method preferably comprises the administration of 500-5000 mg DHA+EPA per day, more preferably 1000-4000 mg per day. DHA is preferably administered in an amount of 400-4500 mg per day, more preferably 750-3250 mg per day. In addition, EPA is preferably administered in an amount of 100-4600 mg per day, more preferably 250-3250 mg per day.

In terms of unit dosage, the proportion of DHA+EPA+DPA (preferably DHA+EPA) of the total fatty acids is preferably 5 to 95 weight %, more preferably 10 to 80 weight %, most preferably 15 to 70 weight %, particularly 15-50 wt %. The composition preferably comprises low amounts of arachidonic acid (AA), preferably less than 5 wt % AA based on total fatty acids, more preferably below 2.5 wt %, most preferably down to 0.5 wt %.

The EPA:DHA weight ratio is preferably in the range of 1:10 and 5:1, particularly 1:5-2:1, more preferably 1:5-1:2. The above-mentioned ratios and amounts take into account and optimise several aspects, including taste (too high LCP levels reduce taste, resulting in a reduced compliance), balance between DHA and precursors thereof to ensure optimal effectiveness while maintaining low-volume formulations. Preferably the weight ratio of DHA:AA is at least 5:1, preferably at least 10:1, more preferably at least 15:1, preferably up to 60:1, more preferably up to 30.

Uridine or Cytidine

The present composition, product, method or kit involves therapeutically effective amounts of uridine, cytidine and/or an equivalent thereof, including salts, phosphates, acyl derivatives and/or esters. In terms of uridine, the composition preferably comprises at least one uridine or an equivalent thereof selected from the group consisting of uridine (i.e. ribosyl uracil), deoxyuridine (deoxyribosyl uracil), uridine phosphates (UMP, dUMP, UDP, UTP), nucleobase uracil and acylated uridine derivatives. In one embodiment, cytidine, CMP, citicoline (CDP-choline) may also be applied. Preferably, the present composition comprises uridine and/or an uridine phosphate selected from the group consisting of uridine monophosphate (UMP), uridine diphosphate (UDP) and uridine triphosphate (UTP); and/or a cytidine phosphate (CMP, CDP, CTP, preferably CMP). Most preferably the present composition the uridine source comprises or consists of uridine (i.e. the ribosyl uracil) and UMP. Preferably at least 50 weight % of the uridine in the present composition is provided by UMP, more preferably at least 75 weight %, most preferably at least 95 weight %. Doses that must be administered are given as UMP. The amount of uracil sources can be calculated taking the molar equivalent to the UMP amount.

The present method preferably comprises the administration of uridine (the cumulative amount of uridine, deoxyuridine, uridine phosphates, nucleobase uracil and acylated uridine derivatives) in an amount of (i) 0.1 to 6 g per day, preferably 0.2 to 3 g per day, more preferably 0.4 to 2 g per day, and/or (ii) 0.1 to 6 g per 100 ml (liquid) composition, preferably 0.2 to 3 g per 100 ml (liquid) composition, more preferably 0.4 to 2 g per 100 ml (liquid) composition. The above amounts also account for any amounts of cytidine, cytidine phosphates and citicoline incorporated in the composition or method.

Choline

The present composition, product, method or kit involves therapeutically effective amounts of choline, a choline salt and/or choline ester. The choline salt is preferably selected from choline chloride, choline bitartrate, or choline stearate. The choline ester is preferably selected from a phosphatidylcholine and lyso-phosphatidyl choline. The present method preferably comprises the administration of more than 50 mg choline per day, preferably 80 to 3000 mg choline per day, more preferably 100 to 2000 mg choline per day, most preferably 150 to 1000 mg choline per day. The present composition preferably comprises 80 mg to 3000 gram choline per 100 ml of the liquid composition, preferably 100 mg to 2000 mg choline per 100 ml, preferably 200 to 1000 mg choline per 100 ml composition, most preferably 200 mg to 600 mg choline per 100 ml. The above numbers are based on choline, the amounts of choline equivalents or sources can be calculated taking the molar equivalent to choline into account.

B Vitamins

The present composition, product, method or kit involves therapeutically effective amounts of at least one vitamin B and preferably at least two vitamins B selected from the group of vitamin B6 (pyridoxine, pyridoxal, or pyridoxamine, or pyridoxine hydrochloride), vitamin B9 (folic acid or folate), and vitamin B12 (cobalamins). Functional equivalents are encompassed within these terms. In particular, good results have been achieved with a combination comprising therapeutically effective amounts of all of vitamin B6, vitamin B12 and vitamin B9.

The vitamin B is to be administered in an effective dose, which dose depends on the type of vitamin B used. As a rule of thumb, a suitable minimum or a maximum dose may be chosen based on known dietary recommendations, for instance as recommended by Institute of Medicine (IOM) of the U.S. National Academy of Sciences or by Scientific Committee on Food (a scientific committee of the EU), the information disclosed herein and optionally a limited amount of routine testing. A minimum dose may be based on the estimated average requirement (EAR), although a lower dose may already be effective. A maximum dose usually does not exceed the tolerable upper intake levels (UL), as recommended by IOM.

If present, the vitamin B6 is preferably present in an amount to provide a daily dosage in the range of 0.1 to 100 mg, in particular in the range of 0.5 to 25 mg, more in particular in the range of 0.5 to 5 mg. The present composition preferably comprises 0.1-100 mg vitamin B6 per 100 g (liquid) product, more preferably 0.5-5 mg vitamin B6 per 100 g (liquid) product, more preferably 0.5-5 mg vitamin B6 per 100 g (liquid) product.

If present, the vitamin B12 is preferably present in an amount to provide a daily dosage in the range of 0.5 to 100 µg, in particular in the range of 1 to 10 µg, more in particular in the range of 1.5 to 5 µg. The present composition preferably comprises 0.5-100 µg vitamin B12 per 100 g (liquid) product, more preferably 1-10 pg vitamin B12 per 100 g (liquid) product, more preferably 1.5-5 µg vitamin B12 per 100 g (liquid) product. The term 'vitamin B12' incorporates all cobalbumin equivalents known in the art.

If present, the vitamin B9 (folic acid) is preferably present in an amount to provide a daily dosage in the range of 50 to 5000 µg, in particular in the range of 100 to 1000 µg, more in particular in the range of 200 to 800 µg. The present composition preferably comprises 50-5000 µg folic acid per 100 g (liquid) product, more preferably 100-1000 µg folic acid per 100 g (liquid) product, more preferably 200-800 µg folic acid per 100 g (liquid) product. Folates include folic acid, folinic acid, methylated, methenylated and formylated forms of folates, their salts or esters, as well as their derivatives with one or more glutamic acid, and all in either reduced or oxidized form.

It is particularly preferred that the composition comprises increased levels of vitamin B6 and vitamin B12 since levodopa reduces B vitamin status and increases plasma total homocystein levels.

Phospholipids

It is preferred to incorporate at least one phospholipid in the composition. The term "phospholipid" excludes PC that is already accounted for in the choline fraction. The present composition preferably comprises at least one phospholipid in an amount of 0.01 to 1 gram per 100 ml, more preferably between 0.05 and 0.5 gram per 100 ml, most preferably 80 to 600 mg per 100 ml. The at least one phospholipid is preferably provided for using lecithin.

Vitamins C, E, Selenium

The present composition, product, method or kit preferably involves therapeutically effective amounts of at least one and more preferably at least two antioxidants selected from vitamin C, vitamin E and selenium.

Vitamin C, or a functional equivalent thereof, may be present in an amount to provide a daily dosage in the range of 20 to 2000 mg, in particular in the range of 30 to 500 mg, more in particular in the range of 75 to150 mg. In one embodiment, vitamin C, or a functional equivalent thereof, is present in an amount in the range of 20 to 2000 mg, in particular in the range of 30 to 500 mg, more in particular in the range of 75 to150 mg per 100 ml of the composition.

Tocopherol and/or an equivalent thereof (i.e. a compound having vitamin E activity) may be present in an amount to provide a daily dosage in the range of 10 to 300 mg, in particular in the range of 30 to 200 mg, more in particular in the range of 35 to 100 mg, to prevent oxidative damage to the injury site resulting from dietary PUFA. In one embodiment, tocopherol and/or equivalent is present in an amount in the range of 10 to 300 mg, in particular in the range of 30 to 200 mg, more in particular in the range of 35 to 100 mg per 100 ml of the composition. The term "tocopherol and/or an equivalent thereof", as used in this description, comprises tocopherols, tocotrienols, pharmaceutical and/or nutritional acceptable derivatives thereof and any combination thereof. The above numbers are based on tocopherol equivalents, recognized in the art.

The present composition preferably contains selenium. The antioxidant activity of selenium advantageously prevents and/or inhibits damages to the brain areas. Preferably the present method provides the administration of a composition comprising 0.01 and 5 mg selenium per 100 ml liquid product, preferably 0.02 and 0.1 mg selenium per 100 ml liquid product. The amount of selenium administered per day is preferably more than 0.01 mg, more preferably 0.01 to 0.5 mg.

The composition, product, method or kit may further comprise proteinaceous material. Should a protein fraction be included, the protein fraction comprises intact proteins, peptides as may be obtained by hydrolyses of intact proteins and by syntheses, derivatives of peptides comprising more than 80 weight % amino acids. In the context of the invention, nitrogen from nucleosides material and choline will not be calculated as being protein.

In one embodiment, it is preferred that the composition has a protein content of less than 15 en %, more preferably less than 10 en %, most preferably less than 5 en % of the total energy content of the composition. The energy percentages of the components are calculated using the calculation factors 9 kcal per g lipid, 4 kcal per g protein or g digestible carbohydrates, 2 kcal per g dietary fibers and zero kcal for the other components in the composition. In one embodiment, it is preferred that the composition comprises less than 0.5 to 10 g protein per 100 ml, more preferably less than 1 to 6 gram protein per 100 ml, most preferably 2 to 6 gram protein/100 ml.

It has been found that enhanced levels of manganese and molybdenum are not necessary in the method according to the invention. The amount of manganese consumed/administered in the method of the invention is preferably less than 300 µg per 100 ml, preferably less than 250 µg per 100 ml, more preferably less than 100 µg per 100 ml, in particular less than 60 µg per 100 ml. In one embodiment, the amount of manganese administered per day is preferably less than 100 µg, more preferably less than 50 µg. In one embodiment, 100 ml liquid composition according to the invention comprises less than 0.05 mg molybdenum, preferably less than 0.025 mg molybdenum.

It is preferred that the amount of taurine (including taurine salts) is less than 0.1 g, preferably less than 0.05 g per daily dose. Additionally or alternatively, it is preferred that the amount of taurine (including taurine salts) is less than 5 mg, more preferably less than 2.5 g per 100 g composition.
In one embodiment, the composition comprises less than 25 mg, more preferably less than 20 mg, most preferably less than 15 mg cysteine and taurine per 100 ml of the (liquid) composition. In one embodiment, the composition comprises less than 25 mg, more preferably less than 20 mg, most preferably less than 15 mg cysteine per 100 ml of the (liquid) composition. It is preferred that the protein fraction comprises more than 70 weight % of casein or caseinates, or hydrolysates thereof, and more preferably 80 weight % or more, because caseins comprise relatively low amounts of cysteine compared to other protein sources. It is further preferred to heat the liquid composition in order to oxidize the cysteine molecules present in the protein. This impairs biological availability of any residual cysteine as present in the formula. A preferred heat treatment involves sterilization. It is preferred to maintain the temperature remains below 135° C., preferably less than 132° C. combined with a sufficient long time to have the cysteine oxidized, i.e. more than 30 seconds, preferably more than 40 seconds.

The nutritional composition preferably further comprises therapeutically effective amounts of (v) dietary fibre. The total daily dosage of dietary fibre in accordance with the invention preferably is 1 to 15 g, more preferably 3 to 12 g, in particular 4-10 g. In terms of total fibre content in a product for use in accordance with the invention the content of the fibre preferably is 1-15 g/100 g, in particular 3-10 g/100 g product. The dietary fibres may be selected from soluble fibres and insoluble fibres. As soluble fibers in the sense of the present invention are preferably understood those that are at least 50% soluble, according to a method described by L. Prosky et al, J. Assoc. Anal. Chem 71: 1017-1023, 1988. The fibres are generally composed of a plurality of carbohydrate units. The fibres may be short-chain (sc) indigestible carbohydrates or long-chain (lc) indigestible carbohydrates. Dependent on the type of fibre, national food regulations may have different definitions for what constitute short chain or long chain. As used herein, short chain fibres generally have a polymerization degree of less than 20, in particular of 2-12, more in particular 3-9; long chain fibres have a polymerisation degree at least one higher than specified for short chain fibres, so 10 or more, 13 or more, or 20 or more.

Parkinson patients may benefit from butyrate-producing fibre. Without being bound by theory, the inventors contemplate that these fibres produce butyrate which is absorbed by the body and provides a neuroprotective effect relevant to improve coordination or body balance. Butyrate-producing fibres are indigestible carbohydrates that have butyrate as a breakdown product when fermented by colonic flora. The term "butyrate-producing fibre" is used herein in particular for fibre that is capable of producing at least 0.5 mmol or more, preferably at least 0.75 mmol or more, more preferably at least 1.0 mmol or more butyrate / gram fibre after 24 hours of in vitro fermentation. In practice, the maximum amount of butyrate producible under these conditions is usually 5 mmol or less, in particular 3.5 mmol or less, more in particular 2.5 mmol or less butyrate / gram fibre after 24 hours of in vitro fermentation.

The producible amount of butyrate is determinable using a semi-dynamic colon model (e.g. using a TIM artificial gut system). In an alternative model, fresh faecal samples are collected from healthy adults (without gastrointestinal problems; no use of antibiotics for a last 2 weeks prior to sample taking). Faecal samples are divided in smaller portions and mixed with glycerol (10%) in an anaerobic cabinet and stored at −80° C. In each experiment the faecal samples from all donors are pooled at equal concentrations and mixed together in an anaerobic cabinet, to avoid subject-dependent variation in the adult microbiota as much as possible. The samples are inoculated with a fibre under fermentation conditions and fermentation is allowed to take place. Butyrate production is determined after 24 hrs using GC. In particular:

the model makes use of samples from four healthy adults (e.g., three male donors and one female donor) in the age of 19-35 years;
the fibre is inoculated in a faeces suspension at a content of 200 mg/ 6 ml faeces suspension;
the faeces suspension is made by mixing faeces with a fermentation medium as 1:5 v/v;
the fermentation medium: buffered peptone water 3.0 g/l, Yeast Extract 2.5 g/l, Tryptone 3.0 g/l, L-Cysteine-HCl 0.4 g/l, Bile salts 0.05 g/l, K2HPO4.3H20 2.6 g/l, NaHCO3 0.2 g/l, NaCl 4.5 g/l, MgSO4.7H20 0.5 g/l, CaCl2. 2H20 0.3 g/l, FeSO4.7H20 0.005 g/l. Ingredients can be added one by one in 800 ml water, pH is adjusted to 6.3±0.1 with K2HP04 or NaHC03 and volume is filled up to 1 liter. Medium is sterilized for 15 minutes at 121° C.;
the fermentation temperature is 37° C.

The total dosage of butyrate producing fibre in accordance with the invention preferably is 1 to 15 g per dosage, more preferably of 2 to 10 g per dosage, in particular 3-8 g per dosage. The total butyrate-producing fibre content, based on total fibre content in a composition for use in accordance with the invention is up to 100 wt %, in particular 99 wt. % or less, more in particular 95 wt. % or less. The total butyrate-producing fibre content, based on total fibre content preferably is at least 50 wt. %, based on total fibre content, preferably at least 70 wt. %, more preferably at least 80 wt. %, in particular 90 wt. % or more.

Preferably the nutritional composition for use according to the invention comprises dietary fibre in an amount sufficient to produce 0.3-5 mmol, more preferably 0.5-3.5, in particular 0.7-3, more in particular 1.0-2.5 mmol butyrate per gram fibre, using a semi-dynamic colon model described above.

Preferred soluble butyrate-producing fibres include fructooligosaccharides (FOS), galactooligosaccharides (GOS), bran and dextrins (e.g. Nutriose®). These are well soluble and are a suitable substrate for colonic flora to produce butyrate, when fermented. Preferred brans are oat bran, rice bran and wheat bran. In a particularly preferred embodiment, several butyrate producing fibres are used, such as a FOS and a dextrin plus optionally bran and/or GOS; or FOS and bran plus optionally dextrin and/or GOS. Good results have been achieved with a combination of short chain FOS, long chain FOS, oat bran, GOS and dextrin. In another preferred embodiment, the combination is part of a nutritional composition that comprises one or more butyrate producing fibres but that is essentially free of GOS.

Preferred insoluble butyrate-producing fibres include resistant starch, such as high-amylose starch or retrograded or RS3 starch. Resistant starch is suitable to provide a particularly high butyrate production per g of resistant starch. Resistant starch is defined to be as those starches which remain intact after digestion during 2 hours in the system of Englyst et al Am J Clin Nutr 1999, 69, 448-454. Commercially available resistant starches are Actistar and Novelose 330. Preferred resistant starches are resistant starches from rice or corn. In a specific embodiment, the resistant starch comprises more than 50 wt % linear polymers of alpha 1,4-glucans which have a degree of polymerization between 10 and 35. Suitable sources of such resistant starches are beans, peas, heat-treated potatoes and heat-treated cereals. Simultaneous presence in the colon of resistant starch and beta glucans, in combination with a xylan will support of growth of the right type of butyrate generating bacteria species.

In a preferred embodiment, the composition for use in accordance with the invention comprises therapeutically effective amounts of vitamin D. An advantage of vitamin D is a reduced balance impairment and reduced risks of falls. In particular, the inventors realized that Parkinson patients benefit from vitamin D with respect to these effects. Good results have been obtained with vitamin D3 (cholecalciferol, calcifediol, calcitriol). If present, the concentration of vitamin D, preferably of vitamin D3, in a nutritional composition for use in accordance with the invention is usually in the range of 5-110 µg/100 g, in particular in the range of 6-85 µg/100 g preferably in the range of 10-50 µg/100 g, more preferably 15-45 µg/100 g product. In the context of the invention, 1 IU of vitamin D is the biological equivalent of 0.025 µg. Hence, 1,000 IU is the biological equivalent of 25 µg.

The composition for use according to the invention usually provides vitamin D in a daily dosage of up to about 50 µg, preferably 25-40 µg. For a liquid product, the vitamin D3 content preferably is 5-85 µg per unit dosage. The unit dosage of a liquid product preferably has a volume of 50-250 ml, in particular 100-150 ml.

In one embodiment, the composition according to the invention comprises per daily dosage or per 125 ml of liquid (preferably water):

200-900 mg, preferably 300-800 mg EPA;
900-1500 mg, preferably 950-1300 mg, more preferably about 1200 mg DHA;
50-600 mg, preferably 60-200 mg, more preferably about 106 mg phospholipids;
200-600 mg, preferably 300-500 mg, more preferably about 400 mg choline;
400-800 mg, preferably 500-700 mg, more preferably about 625 mg uridine and/or UMP (uridine monophosphate);
20-60 mg, preferably 30-50 mg, more preferably about 40 mg vitamin E (alpha-TE);
60-100 mg, preferably 60-90 mg, more preferably about 80 mg vitamin C;
40-80 µg, preferably 45-65 µg, more preferably about 60 µg selenium;
1-5 µg, preferably 2-4 µg, more preferably about 3 µg vitamin B12;
0.5-3 mg, preferably 0.5-2 mg, more preferably about 1 mg vitamin B6; and
200-600 µg, preferably 300-500 µg, more preferably about 400 µg folic acid.

The above liquid composition according to one embodiment of the invention is administered as 125 ml per day. In a preferred embodiment, the nutritional composition preferably further comprises therapeutically effective amounts of (v) dietary fibre, preferably butyrate-producing fibre, more preferably comprising one or more of galacto-oligosaccharides and fructans. The dietary fibre in accordance with the invention preferably is 1 to 15 g, more preferably 3 to 12 g, in particular 4 -10 g per day or per 125 ml liquid composition. The nutritional composition preferably further comprises therapeutically effective amounts of (vi) vitamin D, preferably 10-50 µg, preferably 25-40 µg per day or per 125 ml of liquid product.

The composition as detailed here above was found to improve the efficacy of levodopa in treating motor skills in mammals displaying various symptoms of Parkinson's disease, particularly in terms of motor coordination and balance, and equilibrioception.

Motor skills are movements and actions of the muscles. They are categorized in two groups: gross motor skills and fine motor skills. Gross motor skills involve movement of the arms, legs, feet, or entire body. This includes actions such as running, crawling, walking, swimming, and other activities that involve larger muscles. Fine motor skills are the small movements that occur in the hands, wrists, fingers, feet, toes, lips and tongue. They are the smaller actions that occur such as picking up objects between the thumb and finger, using a pencil to write carefully, holding a fork and using it to eat, and other small muscle tasks that occur on a daily basis. A suitable way to test balancing ability in a mammal (under lab conditions), and thus also to test whether a certain treatment has an effect on a disturbance in equilibrium is a rotarod test, as described in detail in the Examples.

In humans, balance abilities are measured with the Berg Balance Scale (BBS), which is generally considered the gold standard. In one aspect, the treatment thus involves improving coordination and balance according to BBS. The BBS is a clinical measure of a person's static and dynamic balance ability. The test takes 15-20 minutes and comprises a set of 14 simple balance related tasks, ranging from standing up from a sitting position, to standing on one foot. The degree of success in achieving each task is given a score of zero (unable) to four (independent), and the final measure is the sum of all of the scores" (http://aabf.info/pdf/Berg Balance Scale.pdf). The BBS is a validated measure to assess balance abilities in neurological disorders such as Parkinson's disease (Qutubuddin et al., Arch Phys Med Rehabil., 2005, Apr; 85(4): 789-92. Other tests include the Tinetti Mobility test, which assess also risk of falls in Parkinson disease (Kegelmeyer et al., 2007, Phys Ther. 87(10): 1369-78. Fine motor skills can be evaluated in humans using a panel equipped with digital timing sensors, collecting information on speed and accuracy during specific dexterity tasks as described in Smith et al., Neurology, 53(7): 1458- 1458, 1999.

'Coordination' as used herein generally means coordination of limbs. Coordination of limbs can be determined by testing the patient's ability to perform rapidly alternating and point-to-point movements correctly. Point-to-point movements are movements performed with the same index finger to bring from one point to another, for instance from the subject's own nose to the examiner's outstretched finger.

In the context of the present invention, "equilibrioception" could also be worded as 'sense of balance'. The present use or method is thus for improving equilibrioception, which may also be worded as promoting, supporting or stimulating equilibrioception. Equilibrioception can be assessed through a balancing ability test as described here above.

The present invention has been described above with reference to a number of exemplary embodiments. Modifications and alternative implementations of some parts or elements are possible, and are included in the scope of protection as defined in the appended claims.

EXAMPLE

The purpose of the study below was to examine whether there are interactions and/or additive effects between the diet of the invention and levodopa in the intrastriatal rotenone model of Parkinson's disease in mice.

Material and Methods

Mice

Forty-eight seven week-old C57BL/6J mice (Charles River, The Netherlands) were housed at room temperature under a 12 h light/dark cycle. Food and water were provided ad libitum. All animal procedures were approved by the Ethical Committee of Animal Research of Utrecht University, The Netherlands (DEC number 2014.I.12.106).

Surgery

Mice underwent stereotaxic surgery under isoflurane anesthesia: a hole was drilled in the skull and a cannula inserted in the right striatum at the following stereotaxic coordinates: AP +0.4, ML −2.0 from bregma, and DV −3.3 below dura. Rotenone-treated animals were injected with 5.4 µg of freshly prepared rotenone solution (dissolved in 2 µl DMSO). Sham-treated animals were injected with the vehicle (2 µl DMSO). 93 days after surgery the mice were euthanized by decapitation.

Motor Function Test

The motor performance of each mouse was assessed in the Rotarod test as described in Inden et al. *"Neurodegeneration of mouse nigrostriatal dopaminergic system induced by repeated oral administration of rotenone is prevented by 4-phenylbutyrate, a chemical chaperone"* J. Neurochem. 101, 1491-1504 (2007). Briefly, mice were placed on an accelerating rod with speeds starting with 2 rpm and gradually increasing to 20 rpm. Time to first fall was recorded for a maximum of 300 s. The test was performed in order to look at symptom development in time, functional recovery during dietary intervention, and the effects of oral levodopa treatment.

Levodopa Effectiveness in the Rotenone Mouse Model

In order to investigate whether levodopa treatment could effectively improve motor function in the intrastriatal rotenone mouse model for PD, all animals were tested on the rotarod (as described below) 1 h after oral administration of levodopa (20 mg/kg) or vehicle. 30 min before the oral levodopa administration, all animals received a subcutaneous injection of the decarboxylase inhibitor benserazide (6.25 mg/kg). The rotarod tests were performed on days 26 and 27 after surgery, i.e. when rotenone-induced motor dysfunctions were fully developed and before the dietary intervention was started. The order of treatments (levodopa and saline) was balanced according to a Latin square design (Table 1).

TABLE 1

Specification of the order of treatments received by the animals according to a Latin square design.

| allocate | Day 26 | Day 27 |
|---|---|---|
| Sham n = 12 | saline | levodopa |
| Sham n = 12 | levodopa | saline |
| Rotenone n = 12 | saline | levodopa |
| Rotenone n = 12 | levodopa | saline |

The dietary intervention combined with oral levodopa showed to have additive effects on rotarod performance. Performance was assessed on the rotarod (time on rotarod) 60 minutes after administration of 20 mg/kg oral levodopa or vehicle on days 26 and 27 after surgery. Rotenone injection in the striatum negatively affected animals' ability to remain on the rod ($F(1,92)=130.5$, $p<0.0001$), as compared to sham-treated mice. There was an overall effect of levodopa on the animals' motor performances ($F(1,92)=24.77$, $p<0.0001$ for the rotarod test, and an interaction effect between surgery and treatment ($F(1,92)=27.66$, $p<0.0001$).

Diets

Mice were fed either the Control diet (CD) or the Active diet (AD), starting 28 days after surgery, i.e. when motor symptoms plateaued, and continuing for the duration of the experiment. Animals were divided into four groups of 12 animals (Sham+CD, Sham+AD, Rotenone+CD, and Rotenone+AD). Iso-caloric diets were produced by Research Diet Services (Wijk bij Duurstede, The Netherlands) and were based on the CD, i.e. the standard animal food for laboratory rodents AIN-93M30 with 5% fat. For the active diet, uridine (0.51 g/100 g diet) was added and part of the lipid blend of control diet was replaced by fish oil, providing DHA (0.75 g/100 g diet) and EPA (0.50 g/100 g diet). The AD also contained supplementary amounts of choline, phospholipids, selenium, folic acid, and vitamins B6, B12, C, D, and E, above standard levels in the control diet. In addition, the cellulose fibers from the CD were replaced by prebiotic fibers (1.5 g/100 g diet GOS, 0.17 g/100 g diet IcFOS (long-chain), 1.67 g/100 g diet scFOS (short-chain), and 1.67 g/100 g diet nutriose) in the AD.

TABLE 2

Compositions of the experimental diets

| Experimental diets | CD = Control diet (g/100 g) | AD = Active diet (g/100 g) |
|---|---|---|
| Proteins | 14.0 | 14.0 |
| Carbohydrates | 71.0 | 68.7 |
| Fats | 5.0 | 5.0 |
| Soy oil | 1.9 | |
| Coconut oil | 0.9 | 0.2 |
| Corn oil | 2.2 | 1.2 |
| Fish oil | | 3.6 |
| Providing DHA | | 0.75 |
| Providing EPA | | 0.50 |
| Mineral mix (AIN-93M-MX) | 3.5 | 3.5 |
| Vitamin mix (AIN-93-VX) | 1.0 | 1.0 |
| Fibers | 5.0 | 5.0 |
| Cellulose | 5.0 | |
| GOS | | 1.50 |
| lcFOS | | 0.17 |
| scFOS | | 1.67 |
| nutriose (Roquette) | | 1.67 |
| L-cysteine | 0.18 | 0.18 |
| Choline bitartrate | 0.25 | 0.25 |
| Tert-butylhydroquinone | 0.0008 | 0.0008 |
| Uridine | | 0.51 |
| Choline chloride | | 0.40 |
| Soy lecithin | | 0.75 |
| Sodiumselenite | | 0.00023 |
| Pyridoxine | | 0.0041 |
| Folic acid | | 0.00067 |
| Cyanocobalamin | | 0.058 |
| Ascorbic acid | | 0.16 |
| Di-a-tocopherol acetate (500 IU/g) | | 0.47 |
| Cholecalciferol (400,000 IU/g) | | 0.00031 |

Experimental Design

From day 65 after surgery onward, until day 93 (4 weeks in total), animals from the 4 different groups underwent motor function testing once a week after oral administration of saline or one of three doses of levodopa (5, 10, and 20 mg/kg), the order of which was balanced according to a Latin square design (Table 3). All animals received a subcutaneous injection of the decarboxylase inhibitor benserazide (6.25 mg/kg) 30min prior to the oral administration of levodopa. The rotarod test was started 1.5h after benserazide administration and performed as described below.

TABLE 3

Specification of the order of treatments received by the different experimental groups according to a Latin square design.

| Allocate for each experimental group | WEEK 1 | WEEK 2 | WEEK 3 | WEEK 4 |
|---|---|---|---|---|
| n = 3 | saline | levodopa 20 | levodopa 10 | levodopa 5 |
| n = 3 | levodopa 5 | saline | levodopa 20 | levodopa 10 |
| n = 3 | levodopa 10 | levodopa 5 | saline | levodopa 20 |
| n = 3 | levodopa 20 | levodopa 10 | levodopa 5 | saline |

Statistical Analysis

Experimental results are expressed as mean±SEM. Differences between groups were statistically analyzed with a three-way ANOVA, analyzing the effects of the between subject factors surgery (rotenone vs vehicle) and diet (CD vs AD), the within subject factor treatment (levodopa doses 0, 5, 10, and 20 mg/kg), and their interactions. ANOVAs were followed by a Tukey's multiple comparison test when appropriate. For the rotarod test performance over time, data were analyzed with a general linear model repeated measure ANOVA with the within subject factor time and the between subject factors surgery and diet. Results were considered statistically significant when $p<0.05$. Analyses were performed using SPSS 22.0.

Results

Between day 65 and day 93, dose-response relationships for levodopa on behavioral performances were assessed in rotenone- and sham-treated animals. Rotenone treated animals exhibited a deterioration of rotarod performance compared to sham-treated animals ($F(1,176)=425.95$, $p<0.0001$). Rotarod data showed that there was an effect of the diet ($F(1,176)=48.28$, $p<0.0001$) and of levodopa treatment ($F(3,176)=10.40$, $p<0.0001$). Furthermore, there were interaction effects between surgery and diet ($F(1,176)=44.89$, $p<0.0001$), and between surgery and levodopa treatment ($F(3,176)=8.94$, $p<0.0001$). Post-hoc analyses showed that rotenone-treated animals on CD performed significantly better on the rotarod when treated with the highest dose of levodopa (20 mg/kg) compared to animals treated with the lowest dose (5 mg/kg) or saline ($p<0.01$). Within the rotenone-injected mice on AD, animals treated with levodopa 10 or 20 mg/kg had a better ability to remain on the rod than animals on saline or 5 mg/kg ($p<0.001$), showing an additive beneficial effect of levodopa.

Rotenone treated mice on AD performed significantly better than the animals on CD diet at all doses (0, 5, 10, and 20 mg/kg) (all $p<0.05$). The results are plotted in FIG. 1.

Discussion

The study showed therapeutic effects of a specific dietary intervention containing phosphatide precursors uridine and DHA plus additional nutrients that increase membrane phospholipid synthesis and prebiotic fibers, in a mouse model of PD given after full induction of motor symptoms.

The present study demonstrates that the AD combined with oral levodopa treatment is more effective in reducing motor dysfunction (rotarod performance) than the diet or levodopa administered separately. The combined intake of phospholipid precursors including uridine and omega-3 fatty acids such as DHA, can increase brain phospholipid levels, synaptic protein levels, neurite outgrowth, dendritic spine formation, and dopaminergic neurotransmission. The combination of 5 mg/day levodopa together with the intervention diet (AD) yielded rotarod performance that was better than observed even with 20 mg/day levodopa alone. Due to the described effects, the combination of the diet with the drug allows a reduction in the doses given to patients, reducing the negative secondary effects and contributing to a longer beneficial use of the drug.

The AD was also found to have beneficial effects on gastrointestinal functioning in the rotenone model for PD (not shown), and could be hypothesized to improve levodopa uptake and bioavailability with long-term treatment. Since most of PD patients take levodopa orally, a good functioning of the intestinal tract is required in order to absorb the drug at a beneficial rate. Several clinical studies revealed that single or multiple doses of levodopa induced delayed gastric emptying in healthy volunteers and that it might therefore exacerbate the gastrointestinal dysfunction already present in PD patients. Levodopa is absorbed through the duodenum and proximal jejunum by a large neutral amino acid transporter system. Chronic use of oral levodopa is associated with response fluctuations partially due to slow rate of gastric emptying. Delayed gastric emptying in PD patients delays the proper absorption of levodopa, leading to lower blood plasma concentrations of the drug and the occurrence of on-off oscillations. These motor fluctuations, together with dyskinesias are considered as the major side effects of long-term treatment with levodopa.

In summary, the current active diet (AD) was shown to diminish a broad range of PD-like symptoms in a rotenone mouse model. The AD reduced gastrointestinal dysfunction and did not negatively influence the biological effect of levodopa treatment. In fact, the AD had an additive effect to levodopa on motor performance. The above results suggest that this dietary intervention may confer clinical benefits on patients receiving levodopa treatment. Due to the described additive effects, the combination of the diet with the drug may allow a reduction in the doses given to patients, reducing the negative secondary effects and contributing to a longer beneficial use of the drug.

The invention claimed is:

1. A method for (a) treating impaired motor skills in a mammal suffering from Parkinson's Disease; (b) improving the efficacy of levodopa (L-DOPA) in treatment of impaired motor skills in a mammal suffering from Parkinson's Disease (PD); and/or (c) reducing L-DOPA associated involuntary movements selected from the group consisting of choreiform, dystonic and dyskinetic movements, in the treatment of impaired motor skills in a mammal suffering from Parkinson's Disease, the method comprising administering to the mammal therapeutically effective amount of L-DOPA to yield a synergy with a composition comprising therapeutically effective amounts of:
   (i) at least one of uridine and cytidine, or salts, phosphates, acylated forms or esters thereof;
   (ii) at least one of docosahexaenoic acid (22:6; DHA), eicosapentaenoic acid (20:5; EPA) and docosapentaenoic acid (22:5; DPA);
   (iii) choline, or salts or esters thereof; and
   (iv) at least one vitamin B selected from the group consisting of vitamins B6, B9 and B12, wherein the dosage of administered L-DOPA is reduced compared to the dosage of L-DOPA if the composition is not co-administered.

2. The method according to claim 1, wherein the dosage of L-DOPA is reduced by more than 50% compared to the dosage of L-DOPA if the composition is not co-administered.

3. The method according to claim 1, wherein the mammal started to receive L-DOPA less than 5 years before the start of the co-administration.

4. The method according to claim 1, wherein the mammal started to receive L-DOPA less than 2 years before the start of the co-administration.

5. The method according to claim 1, wherein the motor skills comprise motor coordination and balance, and equilibrioception.

6. The method according to claim 1, wherein the component (iv) of the composition comprises at least two vitamins B selected from the group consisting of vitamins B6, B9 and B12.

7. The method according to claim 6, wherein component (iv) of the composition comprises vitamins B6, B9 and B12.

8. The method according to claim 1, wherein the composition further comprises therapeutically effective amounts of (v) dietary fibre.

9. The method according to claim 8, wherein component (v) of the composition comprises therapeutically effective amounts of butyrate-producing fibre.

10. The method according to claim 1, wherein the composition further comprises therapeutically effective amounts of (vi) vitamin D.

11. The method according to claim 1, wherein component (ii) of the composition comprises 500-5000 mg DHA+EPA per day.

12. The method according to claim 1, wherein the composition provides 0.1 to 6 g per day of one or more of uridine and cytidine, or salts, phosphates or esters thereof, calculated as uridine and/or cytidine.

13. The method according to claim 12, wherein the composition providing 0.1-6 g per day of one or more of uridine or salts, phosphates or esters thereof, calculated as uridine.

14. The method according to claim 1, wherein the composition provides, per day, more than 50 mg of choline, or salts or esters thereof, calculated as choline.

15. The method according to claim 1, wherein the composition further comprises therapeutically effective amounts of (vii) at least one antioxidant selected from the group consisting of vitamin C, vitamin E and selenium.

16. The method according to claim 15, wherein component (vii) of the composition comprises therapeutically effective amounts of at least two antioxidants selected from the group consist of vitamin C, vitamin E and selenium.

17. The method according to claim 1, wherein the composition further comprises at least one phospholipid.

18. The method according to claim 1, wherein the composition comprises, per 125 ml of liquid:
   200-900 mg EPA;
   900-1500 mg DHA;
   50-600 mg phospholipids;
   200-600 mg choline;
   400-800 mg uridine and/or UMP;
   20-60 mg vitamin E (alpha-TE);
   60-100 mg vitamin C;
   40-80 µg selenium;
   1-5 µg vitamin B12;
   0.5-3 mg vitamin B6; and
   200-600 µg folic acid.

19. The method according to claim 18, wherein the composition comprises, per 125 ml of liquid:
   300-800 mg EPA;
   950-1300 mg DHA;
   60-200 mg phospholipids;
   300-500 mg choline;
   500-700 mg uridine and/or UMP;
   30-50 mg vitamin E (alpha-TE);
   60-90 mg vitamin C;
   45-65 µg selenium;
   2-4 µg vitamin B12;
   0.5-2 mg vitamin B6; and
   300-500 µg folic acid.

20. A kit of parts for treating impaired motor skills in a mammal suffering from Parkinson's Disease, comprising:
   (a) therapeutically effective amounts of L-DOPA; to yield a synergy with
   (b) a liquid composition comprising therapeutically effective amounts of:
      (i) at least one of uridine and cytidine, or salts, phosphates, acylated forms or esters thereof;
      (ii) at least one of DHA, EPA and DPA;
      (iii) choline, or salts or esters thereof; and
      (iv) at least one vitamin B selected from the group consisting of vitamins B6, B9 and B12.

* * * * *